July 23, 1940. J. H. NICOLAS Plant Pat. 414
ROSE PLANT
Filed March 14, 1940
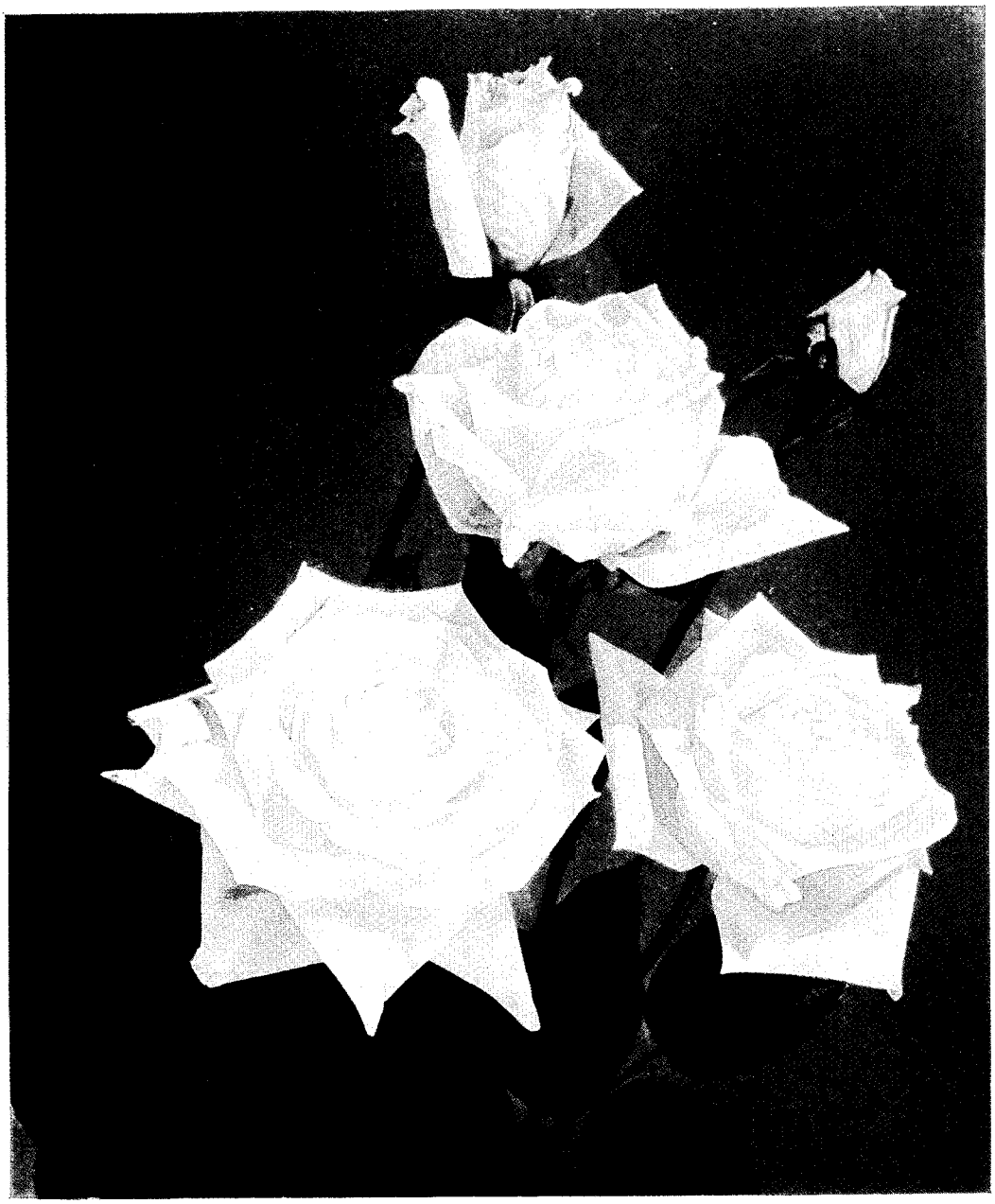
Inventor
Jean H. Nicolas
By Fannie Nicolas
administratrix of the estate
of Jean H. Nicolas, deceased
By Robb & Robb
attorneys Patented July 23, 1940

Plant Pat. 414

UNITED STATES PATENT OFFICE

414

ROSE PLANT

Jean H. Nicolas, deceased, late of Newark, N. Y., by Fannie Nicolas, administratrix, Newark, N. Y., assignor to Jackson & Perkins Company, Newark, N. Y.

Application March 14, 1940, Serial No. 324,008

1 Claim. (Cl. 47—61)

This invention relates to a new and distinct variety of hybrid tea rose plant which is the result of a definite effort to produce improved qualities not found heretofore in a white forcing rose. The new variety originated from the crossing of an unnamed white seedling with the well-known variety White Briarcliff to obtain a combination of the desirable characteristics of these varieties.

The accompanying drawing illustrates the rose in the various stages of development of the flowers, and, as nearly as it is possible to depict, the tones of coloring in these different stages.

The new variety possesses many features of distinctiveness from its parents as well as other varieties, among the most important of which are the slow opening habit and long keeping quality of the flowers, the great number and thin texture of the petals, and the attractive color of the flowers which may be generally characterized as white, very slightly flushed with Marguerite Yellow.

Of further importance is the high productivity of the new variety, as evidenced by definite records of as many as sixteen good cut flowers in the first six months of benching.

With regard to the plant itself, its vigorous habit of growth is especially notable. This is evidenced by the production of long shoots averaging 24 to 30 inches, which are usually followed quickly by two similar breaks after the rose has been cut.

Other features of distinction will be found in a more detailed description of the new variety as follows, in which the color terminology accords with Ridgway's Color Standard.

Parentage: Seedling.
*Seed parent.*—White seedling.
*Pollen parent.*—White Briarcliff.

Classification:
*Botanic and commercial.*—Hybrid tea.

*Flower*

(Observations made at Newark, New York, at one p. m., of January 4, 1940.)

Recurrent—Continuous.

Bud:
*Size.*—Medium.
*Form.*—Ovoid. Is not affected by wet or hot weather.
*Color.*—When sepals first divide—Deep Sea Foam Green, Plate 31. When petals begin to unfurl: top of petal—Sea Foam Green, Plate 31; bottom of petal—Deep Sea Foam Green, Plate 31. When half blown: inside of petals—White, Plate 53, with trace of Marguerite Yellow, Plate 30; reverse of petals—between White, Plate 53, and Marguerite Yellow, Plate 30.
*Sepals.*—Branched. *Color*—Outside—Light Cress Green, Plate 31; inside—Kildare Green, Plate 31. Curl back when bud starts to open.
*Calyx.*—*Shape*—funnel. *Size*—long. *Aspect*—Smooth. *Odor when rubbed*—odorless. *Color*—Cress Green, Plate 31.
*Peduncle.* — *Length* — medium. *Aspect*—smooth. *Color*—Cress Green, Plate 31. *Strength*—erect; slender.
*Opening.*—Bud opens well. Is not affected by adverse conditions.

Bloom:
*Size.*—Large—average size when fully expanded, 5″.
*Borne.*—Several together.
*Stems.*—Long; strong.
*Form.*—When first open—high center. *Permanence*—retains its form to the end except three or four outer petals curl back.
*Petalage.*—Very double (many petals and stamens hidden). Number of petals under normal conditions, 65.
*Color:* Center of flower—between White, Plate 53, and Marguerite Yellow, Plate 30. Outer petals—White, Plate 53, with slight flush of Marguerite Yellow, Plate 30. Base of petals (aiglet)—Deep Sea Foam Green, Plate 31. Inside of petals—between White, Plate 53, and Marguerite Yellow, Plate 30. Reverse of petals—White, Plate 53, with flush of Marguerite Yellow, Plate 30. General tonality from a distance—White, Plate 53.
*Discoloration.*—General tonality at end of first day—White, Plate 53, with flush of Marguerite Yellow, Plate 30. Second day—White, Plate 53, with slight flush of Marguerite Yellow, Plate 30. Third day—White, Plate 53.

Petals:
*Texture.*—Thin. Is not affected by wet or hot weather.
*Appearance.*—Inside and outside—satiny.
*Form.*—Scalloped.
*Arrangement.*—Imbricated (regularly arranged shinglelike). *Petaloids in center*—few; small.
*Persistence.*—Hang on and dry.
*Fragrance.* — Moderate. *Nature* — fruity (Russet apple).
*Lasting quality.*—*On the plant*—long. *As cut flower*—very long.

Genital organs:
*Stamens, anthers.*—Medium size; many. *Color*—Light Cadmium, Plate 4. *Arrangement*—tucked in calyx.
*Stamens, filaments (threads).*—Short. *Color*—Pale Green Yellow, Plate 5.
*Pollen.*—Apricot Yellow, Plate 4.

*Styles.*—Bunched, uneven length; medium length; thin.
*Stigmas.*—Pale Green Yellow, Plate 5.
*Ovaries.*—All enclosed in calyx.
Fruit: Variety has not seeded.

*Plant*

Form: Bush.
Growth: Vigorous; upright.
Foliage: 5 to 7 leaflets.
*Size.*—Medium.
*Quantity.*—Normal.
*Color.*—*New foliage:* upper side—Oil Green center, Plate 5, edges Madder Brown, Plate 13; under side—Rainette Green, Plate 31, edges Madder Brown, Plate 13. *Old foliage:* upper side—Dark Cress Green, Plate 31; under side—Light Cress Green, Plate 31.
*Shape.*—Oval pointed.
*Texture.*—Upper side—flat. Under side—smooth. *Ribs and veins*—light.
*Edge.*—Serrated (saw toothed).
*Serration.*—Single; small.
*Rachis.*—*Color:* upper side—Madder Brown, Plate 13; lower side—Cress Green, Plate 31. *Under side*—Prickles.
*Stipules.*—Short; smooth.
*Disease resistance.*—Resistant.

Wood:
*New wood.*—*Color*—Yellowish Oil Green, Plate 5. *Bark*—smooth.
*Old wood.*—*Color*—Jade Green, Plate 31. *Bark*—smooth.

Thorns:
*Quantity.*—On main stalks from base and on laterals from stalk—ordinary.
*Form.* — Narrow base; medium length, hooked downward.
*Color when young.*—Hay's Russet, Plate 14.
*Position.*—Irregular.

The new variety has been asexually reproduced and the novel characteristics have been found to be established.

What is claimed:

A new and distinct variety of hybrid tea rose plant, characterized as to novelty by its vigorous habit of growth and high productivity of flowers borne on long shoots, which after cutting the flowers quickly develop two similar breaks, by the large number of petals of each flower and the thin texture of the petals, and by the attractive color and long keeping qualities of the flowers and their habit of slowly opening, substantially as shown and described.

FANNIE NICOLAS,
*Administratrix of the Estate of Jean H. Nicolas, Deceased.*